United States Patent [19]

Sanborn et al.

[11] Patent Number: 4,537,780
[45] Date of Patent: Aug. 27, 1985

[54] ALPHA-AMINOOXY ISOVALERATE INSECTICIDES

[75] Inventors: James R. Sanborn; Charles H. Tieman, both of Modesto, Calif.

[73] Assignee: Shell Oil Company, Houston, Tex.

[21] Appl. No.: 662,116

[22] Filed: Oct. 18, 1984

[51] Int. Cl.$^3$ ............... A01N 43/16; A01N 37/34; C07C 121/75; C07D 317/60
[52] U.S. Cl. ............... 514/464; 260/465 D; 514/521; 549/442
[58] Field of Search ............... 260/465 D; 549/442; 424/304, 282

[56] References Cited
FOREIGN PATENT DOCUMENTS 2808317  9/1978  Fed. Rep. of Germany .
 616406  3/1980  Switzerland .

Primary Examiner—Dolph H. Torrence

[57] ABSTRACT

Compounds of the formula

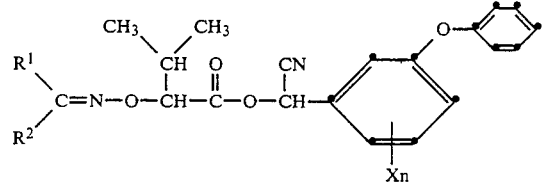

wherein $R^1$ is H or alkyl and $R^2$ is alkyl, alkenyl or phenyl optionally substituted by halogen, (halo)alkyl or methylenedioxy, are useful as insecticides.

13 Claims, No Drawings

ALPHA-AMINOOXY ISOVALERATE INSECTICIDES

BACKGROUND OF THE INVENTION

1. Field of the Invention

The present invention relates to new alpha-aminooxy isovalerates, their use as insecticides and to insecticidal formulations containing these new compounds.

2. Summary of the Invention

The present invention is directed to new alpha-aminooxy isovalerates of the formula I

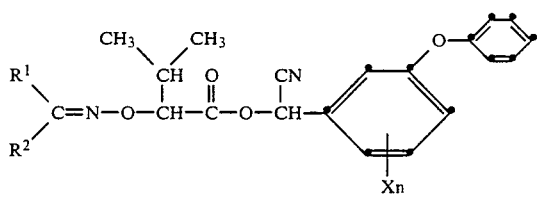

wherein X is a halogen atom; n is 0 or 1; $R^1$ is a hydrogen atom or an alkyl group containing from 1 to 6 carbon atoms; and $R^2$ is an alkyl or an alkenyl group containing up to 6 carbon atoms or a phenyl group optionally substituted by one or more substituents selected from a halogen atom or an alkyl group containing from 1 to 4 carbon atoms optionally substituted by one or more halogen atoms or by a methylenedioxy group. These new compounds are useful as insecticides.

Non-limiting embodiments of species within the scope of the invention include:

Butanoic acid, 3-methyl-2-(((1-(4-bromophenyl)ethylidene)amino)oxy)-, cyano(4-fluoro-3-phenoxyphenyl)methyl ester, Butanoic acid, 3-methyl-2-(((1-(3-(trifluoromethyl)phenyl)ethylidene)amino)oxy)-, cyano(2-methyl-3-phenoxyphenyl)methyl ester.

The halogen atoms used in Formula I include chlorine, fluorine and bromine.

In the Compounds of the Invention, $R^1$ is preferably a hydrogen atom or a methyl group and $R^2$ is preferably a methyl group, a 2-methylpropenyl group or a phenyl group substituted by one or two groups selected from chlorine, fluorine, methyl or trifluoromethyl or by methylenedioxy.

In one embodiment of the Invention, $R^1$ is a hydrogen atom and $R^2$ is a phenyl group substituted by chlorine, trifluoromethyl or methylenedioxy. For example, $R^2$ is 4-chlorophenyl, 2-chlorophenyl, 3,4-methylenedioxyphenyl, 3-(trifluoromethyl)phenyl or the like.

In another embodiment of the Invention, $R^1$ is a methyl group and $R^2$ is 2-methylpropenyl, 4-chlorophenyl, 3,4-methylenedioxyphenyl and the like.

In another embodiment of the Invention, n is 1 and X is a fluorine at the 4-position or n is 0.

The Compounds of the Invention can exhibit geometrical and optical isomerism. The present invention includes all the biologically active compounds of Formula I of the invention and the useful intermediates and, thus includes racemates and various geometric and/or optically-active isomers or mixtures enriched in such isomer forms which may be directly synthesized, resolved or mixed together. The various geometrical and optical isomers of the compounds of Formula I may have different biological activity.

The Compounds of Formula I of the Invention are prepared by conventional esterification procedures known in the art. For example, an alkali metal (potassium) salt of the alpha-aminooxy isovaleric acid in an inert solvent (e.g., acetonitrile) is treated with an alpha-bromo-3-phenoxybenzeneacetonitrile.

The alpha-aminooxy isovaleric acids used as intermediates to the esters of Formula I are prepared by forming the alkali metal salt of an oxime with alkali metal hydroxide in an inert solvent (e.g. toluene) in the presence of a catalyst (including onium catalysts) with azeotropic distillation of the water formed. After the water is removed an alkyl, 2-bromoisovalerate is added and the reaction mixture is refluxed, often for 24–48 hours. The reaction mixture is filtered to remove the salts prior to distillation in a Kugelrohr apparatus. The corresponding carboxylic acids are prepared via alkaline hydrolysis in a ternary mixture of ethanol, tetrahydrofuran and water.

The alpha-aminooxy isovaleric acids are also disclosed and claimed in applicant's concurrently filed U.S. patent application, Ser. No. 662,117.

The oximes utilized in making the acids and alkyl esters intermediates of this invention were prepared from the corresponding oxo compound and hydroxylamine hydrochloride via well known methods, e.g., Vogel, A. I., Practical Organic Chemistry, Wiley and Sons, 1966, p. 343.

The alpha-cyano-3-phenoxybenzyl alcohols and their reactive derivatives are known in the art, e.g., from U.S. Pat. Nos. 3,835,176, 4,218,469, 4,276,306 and the like. Chiral forms of these alcohols and their preparation are also known as in U.S. Pat. No. 4,273,727 and the like. In general, esters of these alcohols have previously been found to have their highest insecticidal activity when the alcohol is in the S-optical configuration. Thus, the preferred esters of the Invention are those in which the alcohol moiety is in the R,S-racemic or S-optical configuration.

ILLUSTRATIVE EMBODIMENTS

The invention is illustrated by the following embodiments which are presented for the purpose of illustration, and should not be regarded as limiting the invention in any way. The identity of the final products, including intermediates, were confirmed by elemental, infrared and nuclear magnetic resonance spectral (NMR) analysis as necessary.

EMBODIMENT 1

Butanoic acid, 3-methyl-2-(((1-(3-(trifluoromethyl)phenyl)ethylidene)amino)oxy-, ethyl ester In a 500 ml round bottom flask fitted with a magnetic stirrer, Dean-Stark trap and nitrogen purge were placed 2.0 g sodium hydroxide in 15 ml of water. To this was added 10.16 g of 3-(trifluoromethyl)acetophenone oxime in 15 ml of toluene and a catalytic amount of tetrabutylammonium hydrogen sulfate and the mixture was heated to reflux overnight. After cooling, 9.75 g of ethyl 2-bromo-3-methyl butyrate was added all at once and the mixture was refluxed for three days. After cooling, the reaction mixture was filtered and the product was distilled in a Kugelrohr appartus to yield 7.33 g of the desired product; b.p. 90° C. (0.05 mm).

EMBODIMENT 2

Butanoic acid, 3-methyl-2-(((1-(3-(trifluoromethyl)phenyl)ethylidene)amino)oxy)-

In a 300 ml round bottom flask equipped with a magnetic stirrer and reflux condenser were placed 15 ml water, 15 ml of tetrahydrofuran, 15 ml of ethanol, 0.6 of sodium hydroxide and 5.0 g of the above ester of Embodiment 1. This mixture was refluxed for 36 hours. The reaction mixture was evaporated to dryness and the residue was taken up in 10% sodium hydroxide. The basic solution was then extracted with methylene chloride to remove neutral products. Acidification of the basic solution and extraction of the aqueous solution with methylene chloride yielded, after drying of the methylene chloride with magnesium sulfate evaporating the solvent, 4.21 g of the desired product; m.p. 49°–51° C.

EMBODIMENT 3

Butanoic acid, 3-methyl-2-(((1-(3-trifluoromethyl)phenyl)ethylidene)amino)oxy)-, cyano(3-phenoxyphenyl)methyl ester In a 300 ml round bottom flask equipped with a magnetic stirring bar, reflux condenser and nitrogen purge were placed 40 ml of acetonitrile, 1.52 g of the above carboxylic acid, 0.69 g of powdered potassium carbonate and a catalytic amount of dibenzo-18-crown-6. This mixture was stirred at room temperature for 15 minutes and then 1.38 g alpha-bromo-3-phenoxybenzeneacetonitrile was added and the reaction mixture was stirred at room temperature overnight. The acetonitrile was evaporated and the residue was taken up into methylene chloride for washing with 10% sodium hydroxide and then drying over magnesium sulfate. The solvent was removed and 1.84 g of the desired product was obtained as a viscous oil.

EMBODIMENTS 4–18

Following procedures similar to those described in Embodiments 1 thru 3 above, additional esters of the invention in which n is 0 were prepared as set forth in Table 1 below.

TABLE I

ESTERS OF FORMULA I.

| Embodiment | $R^1$ | $R^2$ |
|---|---|---|
| 4 | $CH_3$ | $CH_3$ |
| 5 | H | phenyl |
| 6 | $CH_3$ | phenyl |
| 7 | $CH_3$ | $C=C(CH_3)_2$ |
| 8 | $CH_3$ | 4-Cl phenyl |
| 9 | H | 4-Cl phenyl |
| 10 | $CH_3$ | 3,4-methylenedioxyphenyl |
| 11 | H | 3,4-methylenedioxyphenyl |
| 12 | H | 2,4-$Cl_2$ phenyl |
| 13 | H | 2-Cl phenyl |
| 14 | $CH_3$ | 4-$CH_3$ phenyl |
| 15 | H | 4-F phenyl |
| 16 | H | 4-$CF_3$ phenyl |
| 17 | H | 3-$CF_3$ phenyl |
| 18 | $CH_3$ | 3,4-$Cl_2$ phenyl |

The compounds of the invention have been found to be toxic with respect to insects of the class Insecta and the like.

For application, the compound of The Invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of The Invention. The invention also provides a method of combatting pests at a locus, which comprises applying to that locus a compound of The Invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for examle, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspensions concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.001% by weight to as much as about 95% by weight of a compound of The Invention as the active ingredient.

The compositions of the invention may also contain other ingredients, for example, other compounds possessing pesticidal, especially insecticidal, acaricidal or fungicidal properties, as are appropriate to the intended purpose.

Particularly useful compositions can be obtained by using a mixture of two or more kinds of the present compounds, or by the use of synergists, such as those known for the use with the general class of "pyrethroid" compounds, especially alpha-[2-(butoxyethoxy)ethoxy]-4,5-methylenedioxy-2-propyltoluene, also known as piperonyl butoxide, 1,2-methylenedioxy-4-[2-(octylsulfinyl)propyl]benzene, 4-(3,4-methylenedioxyphenyl)-5-methyl-1,3-dioxane, also known as safroxane, N-(2-ethylhexyl)bicyclo[2.2.1]hept-5-ene-2,3-dicarboxamide, octachlorodipropyl ether, isobornyl thiocyanoacetate, and other synergists used for allethrin and pyrethrin. Useful compositions can be prepared with other biological chemicals including cyclopropanecarboxylates, phenylacetates, organic phosphate-type insecticides and carbamate-type insecticides.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insects contacts—is of the order of 0.001 to 0.5% based on the total weight of the formulation, though under some circumstances the effective concentration will be as little as 0.0001% or as much as 2%, on the same basis.

Activity of compounds of The Invention with respect to insect and acarine pests was determined by using standardized test methods to measure the toxicity of the compounds, including the representative tests as follows:

I. Houseflies (*Musca domestica* (Linne)) were tested by placing 50 4- to 5-day old houseflies into a spray cage and spraying with 0.6 ml of a solution of test compound. After spraying, knockdown activity was observed and then the flies were anesthetized with $CO_2$ and transferred to a recovery cage containing a milk pad for food. The cages were held for 18–20 hours after which mortality counts were made. Both dead and moribund flies were counted. The test were conducted employing several different dosage rates for each test compound.

II. Pea aphids (*Acyrthosiphon pisum* (Harris)) were tested by placing about 100 aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Mosquito larvae (*Anopheles albimanus* (Weide)) were tested by placing 10 living and active mosquito larvae in a jar containing a 0.1 ml aliquot of a 1% acetone solution of the test compound thoroughly mixed with 100 ml of distilled water. After 18–22 hours, mortality counts were taken. Both dead and moribund larvae were counted as dead. Larvae which did not swim after being prodded with a needle were considered moribund. The tests were conducted employing several different dosage rates for each compound.

IV. Corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44–46 hours, at which time the dead and moribund larvae were counted. The tests were conducted employing several different dosage rates for each test compound.

The Compounds of the Invention were found to have activity against one or more of the insect species tested.

What is claimed is:

1. A compound of the formula

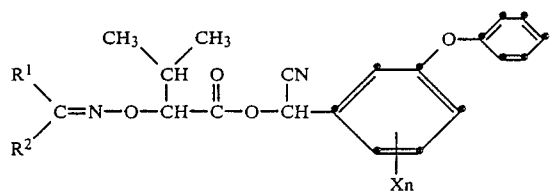

wherein X is a halogen atom; n is 0 or 1; $R^1$ is a hydrogen atom or an alkyl group containing from 1 to 6 carbon atoms; and $R^2$ is an alkyl or an alkenyl group containing up to 6 carbon atoms or a phenyl group optionally substituted by one or more substituents selected from a halogen atom or, an alkyl group containing from 1 to 4 carbon atoms optionally substituted by one or more halogen atoms or by a methylenedioxy group.

2. A compound according to claim 1 wherein $R^1$ is a hydrogen atom or a methyl group.

3. A compound according to claim 2 wherein $R^2$ is a methyl group, a 2-methylpropenyl group or a phenyl group substituted by one or two groups selected from chlorine, fluorine, methyl or trifluoromethyl or by methylenedioxy.

4. A compound according to claim 3 wherein $R^1$ is a hydrogen atom and $R^2$ is a phenyl group substituted by chlorine, trifluoromethyl or methylenedioxy.

5. A compound according to claim 4 wherein $R^2$ is a 4-chlorophenyl group.

6. A compound according to claim 4 wherein $R^2$ is a 3,4-methylenedioxyphenyl.

7. A compound according to claim 4 wherein $R^2$ is 2-chlorophenyl group.

8. A compound according to claim 4 wherein $R^2$ is a 3-(trifluoromethyl)phenyl group.

9. A compound according to claim 3 wherein $R^1$ is a methyl group and $R^2$ is a 4-methylpropenyl group.

10. A compound according to claim 3 wherein $R^1$ is a methyl group and $R^2$ is a 4-chlorophenyl group.

11. A compound according to claim 3 wherein $R^1$ is a methyl group and $R^2$ is a 3,4-methylenedioxyphenyl group.

12. An insecticidal composition comprises an insecticidally effective amount of a compound according to claim 1 and at least one surface-active agent or carrier therefore.

13. A method of controlling insect pests at a locus which comprises applying to the insects or to the locus an insecticidally effective amount of a compound according to claim 1.

* * * * *